United States Patent [19]

Goldsberry

[11] Patent Number: Plant 6,643

[45] Date of Patent: Feb. 28, 1989

[54] DWARF CARNATION PLANT 'SHAVANO'

[75] Inventor: Kenneth L. Goldsberry, Fort Collins, Colo.

[73] Assignee: Colorado State University Research Foundation, Fort Collins, Colo.

[21] Appl. No.: 71,804

[22] Filed: Jul. 10, 1987

[51] Int. Cl.[4] ..... A01H 5/00

[52] U.S. Cl. ..... Plt./71

[58] Field of Search ..... Plt./70–73

*Primary Examiner*—James R. Feyrer

*Attorney, Agent, or Firm*—Edwin L. Spangler, Jr.

[57] ABSTRACT

A carnation plant known by the cultivar name Shavano was developed through a breeding program and is particularly characterized as to uniqueness by its dwarf growth habit and the following combined characteristics: upon pinching a rooted cutting, forms 3 to 6 lateral stems 21 to 26 cm long, each developing a terminal flower and secondary buds which open intermittently after the terminal flowers seneses; dark pink flowers 4.5 to 6.0 cm in diameter with an intense clove fragrance; can be grown under specified environmental conditions either as a single pinched plant per 10 cm pot or 3 pinched plants per 13 cm pot, which results in an ideal new flowering house plant.

1 Drawing Sheet

1

My present invention relates to a new and distinct dwarf cultivar of *Dianthus caryophyllus* Linn. identified as plant 85-215-116 and given the name Shavano.

Shavano is a product of a breeding program started by me at Colorado State University in 1974, using commercially available semi dwarf germplasm, crossing selected unnamed seedlings and incorporating various known carnation germplasm with an objective of creating dwarf carnation cultivars that could be asexually produced for commercial use, in controlled environments, as flowering house plants.

Shavano was originated from a cross made in a controlled breeding program at the Horticulture Department, W. D. Holley Plant Environmental Research Center, Colorado State University, Fort Collins, Colo. using the unnamed seed parent 83-15-20 and an unnamed pollen parent 82-43A, also developed by the present inventor.

Shavano was discovered and selected as one flowering plant within the progeny of the stated cross by Kenneth L. Goldsberry on July 24, 1985 in a controlled environment in Fort Collins, Colo.

The first act of asexual reproduction of Shavano was accomplished when vegetative cuttings were taken, by the inventor, from the initial selection on Sep. 5, 1985 in a controlled environment in Fort Collins, Colo. The initial rooting of the cuttings and performance of the resulting plants have demonstrated that the distinctive characteristics of this new cultivar Shavano, here in disclosed, appear to be firmly fixed and hold true from generation to generation.

Shavano has not been observed under all possible environmental conditions. The phenotype may vary significantly with variation in the production environment including irrigation regimes, temperature, light intensity, day length and nutritional programs. It has been observed and evaluated, from a rooted cutting to a mature plant while being grown in Fort Collins and Denver Colo. and Encintias and Salinas, Calif. under greenhouse conditions, which approximate those generally used in commercial practice.

2

The following traits, which have been repeatedly observed, characterize Shavano and distinguishes it as a new and distinct dwarf carnation cultivar:

1. Somatic chromosome is 2n=30
2. A double type flower, similar to commercial cut flower spray types
3. Flower sizes range from 4.5 to 6.0 cm in diameter
4. Dark pink flower color
5. Medium flowering response on a scale of early, medium or late flowering
6. Three to six lateral shoots develop following a pinch of the main stem
7. The terminal flower, four to five secondary buds and four to six tertiary buds form on each flowering stem. As the terminal flowers senese, the secondary buds continue to open, the tertiary buds usually abort
8. Secondary peduncle lengths on a single stem varies between 1.5 to 13.3 cm
9. Plant height ranges between 21.0 to 26.0 cm
10. Heavy clove fragrance p There are no dwarf carnation cultivars, for house plant use, presently developed and known to the inventor.

BRIEF DESCRIPTION OF THE DRAWING

The accompanying top colored photograph taken on June 19, 1987, using an 18 percent Kodak photographic gray card as a color base, illustrates in perspective view and the overall appearance of Shavano (85-215-116) grown in 10 cm (single plant) and 15 cm (3 plants) azalea pots. The bottom photo shows buds, inflorescence, stem, foliage characteristics and color of Shavano are typical and true as possible with illustrations of this type.

The following detailed description of my new dwarf carnation cultivar are based upon observations of greenhouse grown plants made in 1986 at Fort Collins, Colo. The color values were determined in a standard color viewing booth with a 5000° K. fluorescent light source using references developed and published by The Royal Horticultural Society, London, England.

PLANT CHARACTERISTICS

Origin: Seedling selection.

Parentage:

*Seed parent.*—Selected unnamed seedling, 83-15-20 (Goldsberry).

*Pollen parent.*—Selected unnamed seedling 82-43A (Goldsberry).

Classification:

*Botanic.*—*Dianthus caryophyllus* Linn. cv. Shavano.

*Commercial.*—Dwarf carnation for pot plant production.

Propagation: Vegetative cuttings, 6 to 8 cm. in length initiate visible roots in 8 to 10 days in the winter and 5 to 8 during the summer, when rooted under mist in a rooting medium temperature of 20° C. A quality rooted cutting with an abundance of roots, is usually ready to plant in 15 days in the summer and 18 to 20 in the winter.

Growth habit: Three to six lateral shoots form naturally, but are accelerated by removing the terminal portion of the main stem, at the sixth or seventh node from the top, resulting in a compact, bushy and strong up right plant. Some basal branches may elongate enough to place apical buds on a plane approximating the terminal flowers of the initial stems.

Stems: Numerous lateral branches form close to the base of the plant and vary in length from 21–26 cm, having 6 to 10 nodes with opposite leaves. A reproductive bud usually forms at each upper 5 to 6 nodes. Shoots forming at the seventh or tenth node below the terminal flower, usually develop into another flowering stem in proper environmental conditions. All stems have a blue-grey glaucous condition, approximating 189B in color.

Foliage: Leaves are abundant and typical of the commercial carnation type. The leaves at the sixth node form the top of each stem range in length from 10.5 to 13.5 cm and have an average width of 1.1 cm, but are progressively smaller above and below these nodes. Both the upper and lower sides of the leaves are dark green and have a blue-grey glaucous condition. The color of both surfaces is identified as 189B with the surface bloom present and 137A when it is removed.

INFLORESCENCE CHARACTERISTICS

Buds: Terminal buds average 2.8 cm in length just prior to opening and the secondary buds 2.6 to 3.0 cm. The average bud circumference ranges from 5.1 cm for the terminal and secondary buds 4.6 cm, at the first sign of petal color. Significantly visible tertiary buds form on the peduncles of the upper five secondary buds, but do not open in low light conditions. Buds are oval in shape and pointed.

Sequence of development: The terminal bud on each stem will show color before any lateral bud color is visible. The opening sequence of the secondary buds is inconsistent but is generally at node positions, two, one, three and four from the terminal flower position on each stem. In the proper environments, new flower bearing shoots emerge from the seventh to tenth nodes below the terminal flower and at the base of the plant, creating a perpetual flowering plant in high light conditions.

Flowering response: A rooted cutting pinched 2 to 4 weeks after planting will flower 13 to 16 weeks following the pinch from a October 1 plant date and 11 to 12 weeks from a June 1 date in Fort Collins, Colo. when growing temperatures approximate 11° C. at night and 17° C. during the day.

Inflorescence type: Each initial stem is a semi-compound spray with a terminal bud, 5 to 6 secondary and 5 to 6 tertiary buds and 2 to 5 lateral shoots.

Number of buds and flowers per stem: Each stem has a terminal flower that develops along with the upper most, of the 5 to 6 secondary buds; new flowering shoots usually form at the seventh to tenth nodes of each initial stem resulting in an average potential of 30.0 flowers per stem. A total of 90 to 180 buds and flowers can be on a single plant at one time. The tertiary buds do not develop petals in low light and therefore do not open.

Peduncle length: The length of the peduncles range from 1.5 cm for the top secondary bud to 13.3 cm for the lowest bud, on each stem, when the terminal flower is in prime condition. The peduncles of the tertiary buds vary from 0.7 to 5.0 cm.

Peduncle strength: Strong, holds flowers erect during all growing seasons; degree of brittleness is related to environmental conditions.

Flower:

*Size.*—Terminal flowers range in size from 5.0 to 6.0 cm and the secondaries, 4.5 to 5.6 cm depending on the environment.

*Type.*—Commercial double with 41 to 53 moderately serrated petals in the terminal flowers, which have an average length and width of 4.4 cm and 2.6 cm, respectively.

*Form.*—Sub hemispherical in longitudinal section with the petals adjacent to the calyx, slightly reflexed at maturity. Seldom splits. The secondary flowers are 4.5–5.6 cm in diameter and have average petal lengths of 4.4 cm and 2.6 cm wide. The tertiary buds do not open.

Corolla color: General tonality at a distance of 1 meter; 63D at petal margins. Upper petal surface: newly opened petals are 63D in color, at the margins, 63C in the middle area and 63D at the base. Lower petal surface: have the same color characteristics as the upper surface.

Keeping quality: In the greenhouse, individual flowers remain aesthetically pleasing up to 6 days; in the home 8 to 10 days with room temperatures of 17° C. and high, natural light intensity.

Fragrance: Intense fragrance which increases with temperature.

Reproductive organs:

*Androecium.*—Typical carnation except has 16–32 filaments, with aborted anthers, there is no pollen.

*Gynoecuim.*—Typical of carnation in all respects; pistil is 0.7 to 1.1 cm in length and has 3 to 4 styles and stigmas. The pistil is irregularly grooved, similar to that of Sneffels. The stigmas are white at all stages of maturity.

Disease resistance: The plant has been found free of pathogen races currently associated with standard carnation cultivars, including the wilts and Etched Ring or Fleck viruses.

I claim:

1. A new and distinct cultivar of *Dianthus caryophyllus,* Linn, identified as 85-215-116 and known as Shavano and substantially as herein described and illustrated.

* * * * *

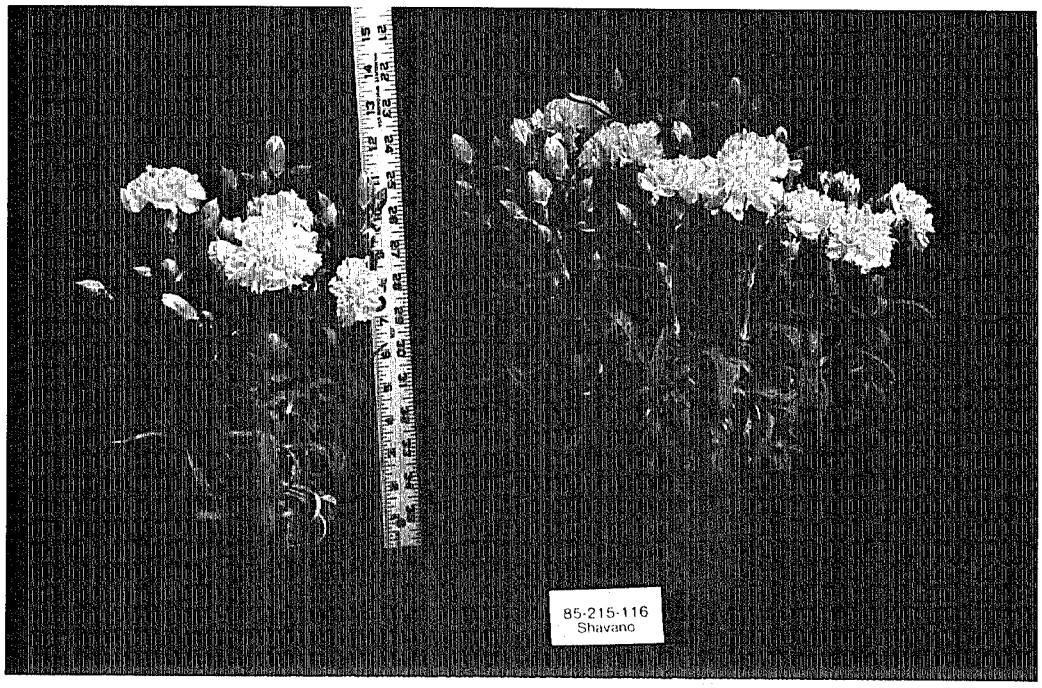
85-215-116
Shavano
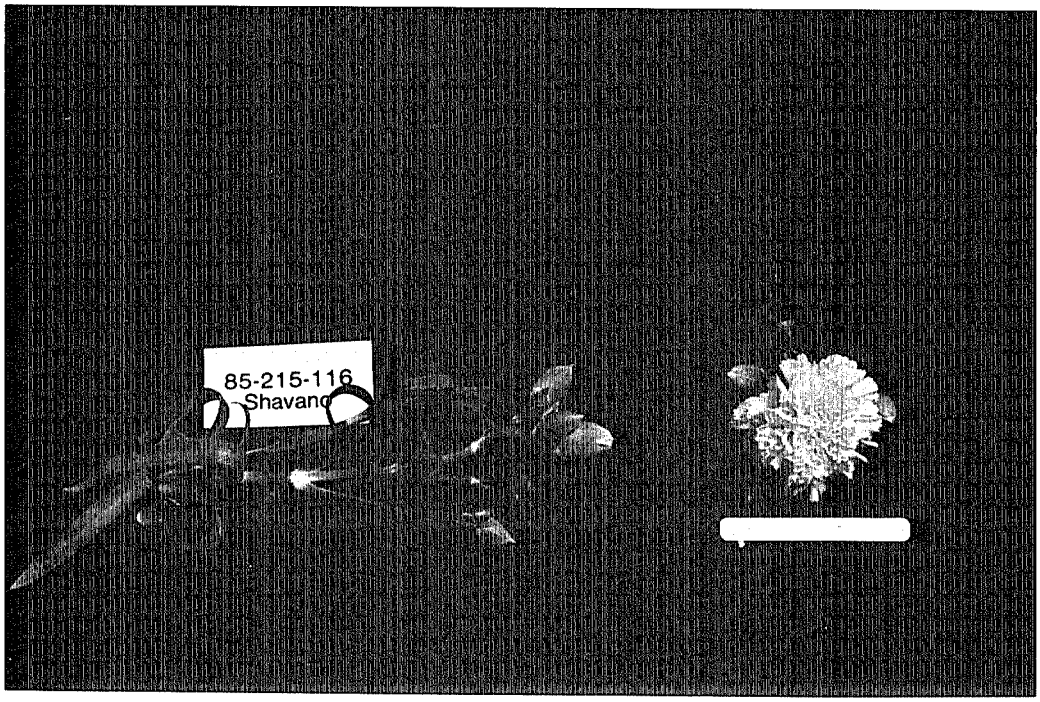
85-215-116
Shavano